United States Patent [19]
DeAngelis et al.
[11] Patent Number: 4,510,888
[45] Date of Patent: Apr. 16, 1985

[54] SHIELD ASSEMBLY FOR AN AREA OF AN ANIMAL TO BE PROTECTED

[76] Inventors: Barbara DeAngelis, 1218 80th St., Brooklyn, N.Y. 11228; Howard Jacobsen, 190 72nd St.; Edwin Jacobsen, 4 Bayridge Pl., both of Brooklyn, N.Y. 11209

[21] Appl. No.: 333,648

[22] Filed: Dec. 23, 1981

[51] Int. Cl.[3] ........................ B68C 5/00; A01K 29/00; A61F 13/00

[52] U.S. Cl. ........................................ 119/143; 54/82; 128/88; 128/132 R

[58] Field of Search ............... 54/82, 80; 119/96, 126, 119/127, 128, 142, 143; 128/87 R, 88, 89 R, 90, 402, 132 R

[56] References Cited

U.S. PATENT DOCUMENTS

| | | | |
|---|---|---|---|
| 97,896 | 12/1869 | Eager | 54/80 |
| 1,880,945 | 10/1932 | Ettinger | 128/87 R |
| 2,194,921 | 3/1940 | Wagner, Jr. | 54/82 |
| 2,947,307 | 8/1960 | Hoppe | 128/90 |
| 3,209,517 | 10/1965 | Hyman | 119/143 |
| 3,439,673 | 4/1969 | Sprecher | 119/127 |
| 4,191,373 | 3/1980 | Lancellotti | 128/88 |

FOREIGN PATENT DOCUMENTS

| | | | |
|---|---|---|---|
| 191055 | 3/1967 | U.S.S.R. | 128/89 R |

*Primary Examiner*—Stephen C. Pellegrino
*Assistant Examiner*—J. L. Kruter
*Attorney, Agent, or Firm*—Louis E. Marn

[57] ABSTRACT

There is disclosed a protective shield assembly for positioning about an area of an animal to be protected and comprised of semicylindrically-shaped sections or elongated sleeve members hingeable mounted to one another and provided with inwardly extending mounting elements for supportably engaging portions of the leg of the animal about the area to be protected.

8 Claims, 4 Drawing Figures

FIG. 1
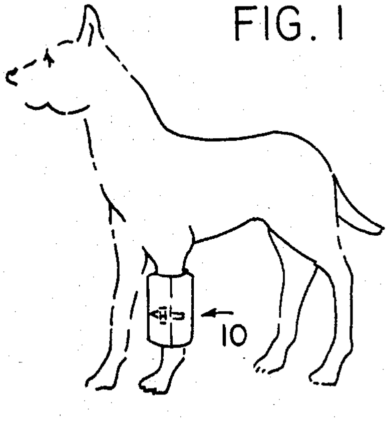
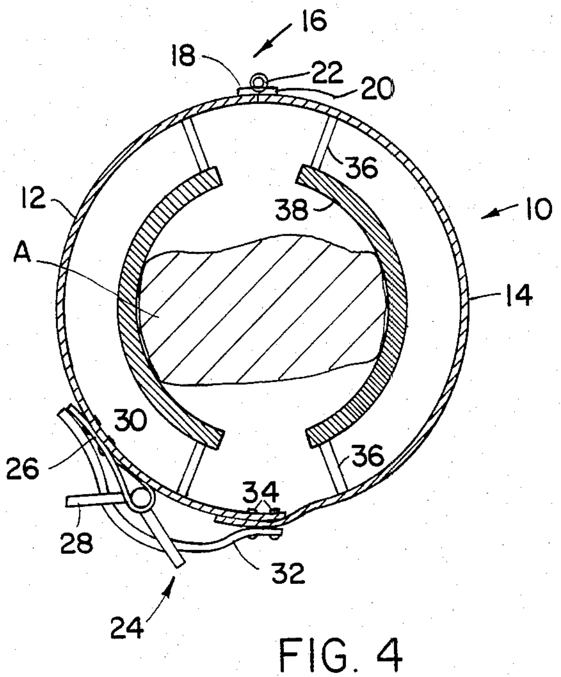
FIG. 4
FIG.2
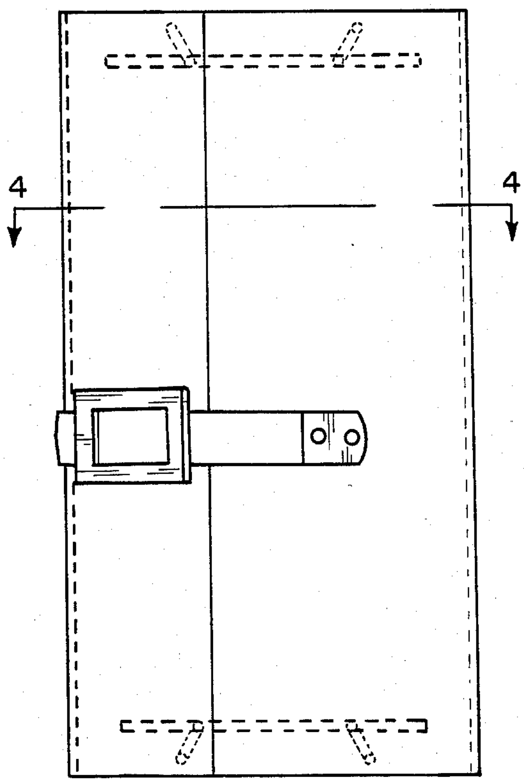
FIG.3
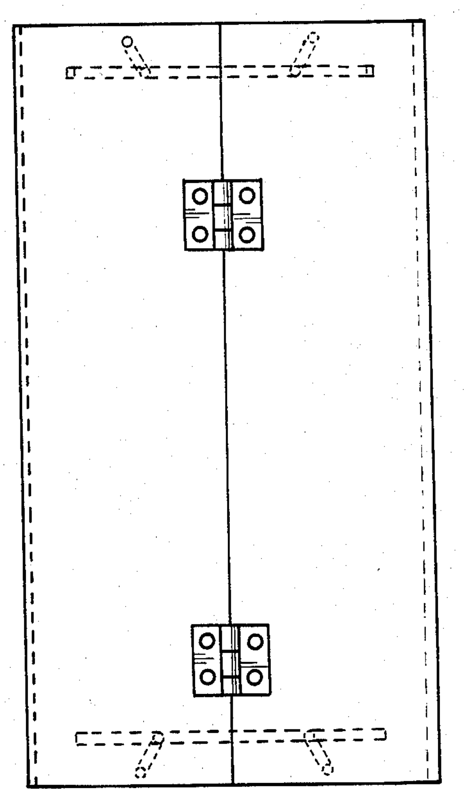

SHIELD ASSEMBLY FOR AN AREA OF AN ANIMAL TO BE PROTECTED

FIELD OF THE INVENTION

This invention, in general, relates to an animal protective assembly, and more particularly to a protective shield assembly for encircling and protecting the leg of an animal, particularly a canine, to permit healing of a wound and to substantially prevent continued self-destruction of the healing process.

BACKGROUND OF THE INVENTION

Injury to animals, such as canines, occurs inter alia by the intervention of outside forces, such as a vehicle, or by accidentally running into a standing obstacle, such as a tree. Additionally, epidermal problems, such as dry skin, rashes and the like may cause locallized problems which by natural tendencies, the animal attempts to treat by biting or licking to alleviate the discomfort associated with the injury or skin condition. It has been observed that animals, such as canines, may particularly aggravate a situation to the point where surgical procedure or destruction is necessitated.

Further, during the post-treatment, an animal has a tendency to gnaw, chew or otherwise get at the injury location which may have stitches, topical dressings or other medicinal treatment applied for healing purposes. Such action by the animal tends to inhibit and prolong the recuperative period and may lead to infection of the injured site.

In U.S. Pat. No. 3,791,383 to Friedman, there is disclosed an injury protection device for quadropods or four-legged animals comprised of a tubular member having transversely opposed cut-out sections including harnessing means for securely attaching the device to the animal. The cut-out sections are adapted to enable the leg joints to have complete mobility, such that the movement of the animal is unimpaired. The device permits of venting the injury to the atmosphere to facilitate healing of the injury. The assembly tends to effect a rubbing of the skin about the support portion as well as portions about the leg over which the device is positioned thereby aggravating the recuperative period.

OBJECTS OF THE INVENTION

An object of the present invention is to provide an improved protective shield for an animal.

Another object of the present invention is to provide an improved protective shield for an animal permitting of facile positioning.

Yet another object of the present invention is to provide an improved protective shield for an animal of simplified construction.

Still another object of the present invention is to provide an improved protective shield for an animal permitting substantially unimpaired movement by the animal.

SUMMARY OF THE INVENTION

These and other objects of the present invention are achieved by a protective shield assembly comprised of semicylindrically-shaped members hingeably mounted to one another and provided with inwardly extending mounting elements for supportably engaging portions of the leg of the animal.

BRIEF DESCRIPTION OF THE DRAWINGS

The invention will be more clearly understood by reference to the following detailed description of an exemplary embodiment thereof when taken in conjunction with the accompanying drawing wherein:

FIG. 1 is a pictorial representation of the protective shield assembly of the present invention positioned on a leg of a canine;

FIG. 2 is a plan view of the protective shield assembly of the present invention;

FIG. 3 is a back view of the protective shield assembly of FIG. 2; and

FIG. 4 is a side view thereof.

DETAILED DESCRIPTION OF THE INVENTION

Referring now to the drawing, and in particular to FIGS. 1 to 4, there is illustrated a protective shield assembly of the present invention, generally indicated as 10, and comprised of semicylindrically-shaped half sections or sleeve members 12 and 14 hingeably mounted to one another by hinge members, generally indicated as 16. The hinge members are comprised of half hinge elements 18 and 20 mounted, such as by welding, to the respective semicylindrically-shaped half sections or sleeve members 12 and 14 and maintained in hinged relationship by hinge pin 22.

The protective shield assembly 10 is formed with a securing assembly, generally indicated as 24, and comprised of a looped strap 26 including a buckle 28, mounted such as by rivets 30 to the member 12, and by a strap 32 mounted, such as by rivets 34 to the member 14.

Proximate the ends of the protective shield assembly 10 and mounted to inner surfaces of the members 12 and 14, such as by welding, there are provided inwardly-extending arm members 36. A semicircularly-shaped support member 38 is mounted to paired arm members 36 in a manner to engage the leg of the animal, such as illustrated in FIG. 4. The semicircularly-shaped support members 38 are preferably formed of a metal or plastic overlayed with a protective outer layer of a resilient material, such as rubber, foamed rubber of the like.

The members 12 and 14 may be formed of a metal, such as aluminum or stainless steel, or may be formed of a thermoplastic material, such as polycarbonate or like plastic material having physical properties to withstand the effects of gnawing or chewing by the animal. It will be understood by one skilled in the art that the hinge assemblies 16, buckle assembly 24, arm members 26, etc. are secured to the members 12 and 14 by means compatible with the materials of construction of the members 12 and 14. Additionally, while the semicylindrically-shaped members are illustrated as being formed of a curved surface, the surface may be corrugated or formed of a plurality of planar surfaces. Still further, while a universal protective shield assembly would be desirable for any size animal, the protective shield assemblies of the present invention are made in varying lengths and of varying spacial distances between the support member 38 and the members 12 and 16.

In operation, the injury to the animal is first cleaned and treated with an antiseptic material and a normal active treatment protocol performed whereupon the protective shield assembly 10 of the present invention is caused to be encircled about the treated area of the leg of the animal in a manner such that the treated area is positioned between the semicircularly-shaped support members 38, i.e. out of contact with the treated area to minimize aggravation to the injury wound. The strap 32 is positioned within the buckle 28 and drawn fast to a point whereby the force between the support elements 38 and the leg of the animal is sufficient to maintain the protective shield assembly 10 of the present invention at the desired position but with a support force that is insufficient to cause discomfort to the animal or to aggravate the treatment protocol by reducing circulation to the injury or wound.

While the invention has been described in connection with an exemplary embodiment thereof, it will be understood that many modifications will be apparent to those of ordinary skill in the art and that this application is intended to cover any adaptation or variation thereof; therefore, it is manifestly intended that this invention be only limited by the claims and the equivalent thereof.

What is claimed is:

1. A protective shield assembly for positioning on a limb of an animal about an area to be protected from access by the animal to such area, which comprises:

elongated sleeve member means including an inner surface wherein said sleeve member means are mounted to one another which when applied to said limb of said animal define a chamber in a closed position;

arm member means positioned and secured to said inner surface of at least one of said sleeve member having arm means extending radially inwardly into said chamber and including are shaped means for contacting said limb of said animal; and means for securing said elongated sleeve member means to one another about said limb of said animal proximate said area to be protected, said elongated sleeve member means being in spaced apart relationship to said area to be protected of said limb of said animal within said chamber thereby defining an opened zone between said elongated sleeve member means and said area to be protected to prevent animal access to the area to be protected and allow for healing of a wound in said protected area.

2. The protective shield assembly as defined in claim 1 wherein said elongated sleeve members are semicylindrically-shaped members formed with a curved surface.

3. The protective shield assembly as defined in claim 1 and including half hing members mounted to each of said elongated sleeve members and a hinge pin for hingeably engaging said half hinge members.

4. The protective shield assembly as defined in claims 1, 2 or 3 wherein said means for contacting said leg of said animal are semicircularly-shaped elements mounted to said arm members.

5. The protective shield assembly as defined in claim 4 wherein said arm members are disposed proximate end portions of said elongated semicylindrically shaped members.

6. The protective shield assembly as defined in claim 1 wherein said securing means includes a buckle and a strap member.

7. The protective shield assembly as defined in claim 1 wherein said elongated sleeve members are formed of a metal.

8. The protective shield assembly as defined in claim 1 wherein said elongated sleeve members are formed of a plastic.

* * * * *